(12) United States Patent
Waki et al.

(10) Patent No.: US 8,608,659 B2
(45) Date of Patent: Dec. 17, 2013

(54) ULTRASONIC IMAGING APPARATUS

(75) Inventors: Kouji Waki, Chiba (JP); Takashi Osaka, Chiba (JP); Mitsuaki Ito, Chiba (JP); Takeshi Matsumura, Chiba (JP); Naoyuki Murayama, Chiba (JP); Takashi Kashiwagi, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1311 days.

(21) Appl. No.: 10/580,100

(22) PCT Filed: Nov. 11, 2004

(86) PCT No.: PCT/JP2004/016747
§ 371 (c)(1),
(2), (4) Date: May 19, 2006

(87) PCT Pub. No.: WO2005/048847
PCT Pub. Date: Jun. 2, 2005

(65) Prior Publication Data
US 2007/0112270 A1    May 17, 2007

(30) Foreign Application Priority Data
Nov. 21, 2003   (JP) ................................ 2003-391997
Nov. 25, 2003   (JP) ................................ 2003-393305

(51) Int. Cl.
*A61B 8/00*    (2006.01)
(52) U.S. Cl.
USPC ........................................................ 600/437
(58) Field of Classification Search
USPC ........................................................ 600/437
See application file for complete search history.

(56) References Cited

U.S. PATENT DOCUMENTS

| 6,068,597 | A * | 5/2000 | Lin ................................ 600/443 |
| 7,245,746 | B2 * | 7/2007 | Bjaerum et al. ............... 382/128 |
| 7,455,640 | B2 * | 11/2008 | Suzuki et al. .................. 600/437 |
| 2004/0234113 | A1 * | 11/2004 | Miga .............................. 382/128 |
| 2006/0052702 | A1 * | 3/2006 | Matsumura et al. ........... 600/443 |

FOREIGN PATENT DOCUMENTS

| JP | 05-168631 | 7/1993 |
| JP | 09-182751 | 7/1997 |

(Continued)

OTHER PUBLICATIONS

Nitta, Naotaka, "Experimental Investigation of Tissue Elasticity Reconstruction Based on the Measured 3-D Displacement Vector", J Med Ultrasonics, Apr. 15, 2000, vol. 27, No. 4, p. 738.

(Continued)

*Primary Examiner* — Tse Chen
*Assistant Examiner* — Hien Nguyen
(74) *Attorney, Agent, or Firm* — Antonelli, Terry, Stout & Kraus, LLP.

(57) ABSTRACT

An ultrasonic imaging apparatus according to the present invention includes an ultrasonic probe (2) for receiving and transmitting ultrasonic waves from/to an object (1), ultrasound image structuring means (6) for generating an ultrasound image from a reflected echo signal received by the ultrasonic probe, elastic image structuring means (7) for obtaining a physical quantity of the elasticity of a region of the object corresponding to the ultrasound image from the reflected echo signal and generating a color elastic image, display means (9) for overlaying the ultrasound image to the color elastic image, or arranging the ultrasound image and the color elastic input means (17) for variably setting a corresponding relationship between a hue of the color elastic image and the level of the physical quantity displayed on the screen. The level of the elasticity, such as the strain of each region in the tissue or an elastic modulus, is displayed with colors in accordance with the interest of the examiner, thus improving the convenience of use.

9 Claims, 13 Drawing Sheets

(56) References Cited

FOREIGN PATENT DOCUMENTS

| | | |
|---|---|---|
| JP | 2000-060853 | 2/2000 |
| JP | 2003-275211 | 9/2003 |

OTHER PUBLICATIONS

Japanese Office Action dated Aug. 24, 2010, issued in corresponding Japanese Patent Application No. 2005-515588.

* cited by examiner

| | R | G | B |
|---|---|---|---|
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| 32 | 0 | 255 | 0 |
| | 0 | 255 | 0 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |

(b)

| | R | G | B |
|---|---|---|---|
| | 255 | 0 | 0 |
| | 255 | 0 | 0 |
| | 255 | 0 | 0 |
| 32 | 0 | 255 | 0 |
| | 0 | 255 | 0 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |
| | 0 | 0 | 255 |

(c)

| | R | G | B |
|---|---|---|---|
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| | 255 | 0 | 0 |
| 32 | 0 | 255 | 0 |
| | 0 | 255 | 0 |
| | 0 | 0 | 255 |
| | 0 | 0 | 255 |
| | 0 | 0 | 255 |

| RANGE OF CALCULATING VALUE OF ELASTIC MODULUS | | R | G | B |
|---|---|---|---|---|
| 2801~3500 | ↑ | 255 | 255 | 255 |
| 2401~2800 | ↑ | 255 | 255 | 255 |
| 2001~2400 | ↑ | 255 | 255 | 255 |
| 1801~2000 | ↑ | 255 | 255 | 255 |
| 1601~1800 | ↑ | 255 | 255 | 255 |
| 1501~1600 | ↑ | 255 | 255 | 255 |
| 1401~1500 | ↑ | 255 | 255 | 255 |
| 1301~1400 | ↑ | 255 | 255 | 255 |
| 1201~1300 | ↑ | 255 | 255 | 255 |
| 1101~1200 | ↑ | 255 | 255 | 255 |
| 1001~1100 | ↑ | 100 | 100 | 100 |
| 901~1000 | ↑ | 100 | 100 | 100 |
| 801~900 | ↑ | 0 | 0 | 0 |
| 701~800 | ↑ | 0 | 0 | 0 |
| 601~700 | ↑ | 0 | 0 | 0 |
| 501~600 | ↑ | 0 | 0 | 0 |
| 401~500 | ↑ | 0 | 0 | 0 |
| 301~400 | ↑ | 0 | 0 | 0 |
| 201~300 | ↑ | 0 | 0 | 0 |
| 101~200 | ↑ | 0 | 0 | 0 |
| 0~100 | ↑ | 0 | 0 | 0 |

ULTRASONIC IMAGING APPARATUS

TECHNICAL FIELD

The present invention relates to an ultrasonic imaging apparatus that displays an ultrasound image of a diagnostic portion of an object with ultrasonic waves. In particular, the present invention relates to a technology for displaying an elastic image with the strain of the tissue or an elastic modulus.

BACKGROUND ART

An ultrasonic imaging apparatus measures an ultrasonic reflectance of the tissue in an object with ultrasonic waves. In general, the ultrasonic imaging apparatus displays an ultrasound image of the reflectance of a diagnostic portion with the measured value, as luminance. Recently, in the ultrasonic imaging apparatus, time-series images of the temporal change in the tissue are obtained upon applying a pressure to the measured portion, the correlation between the time-series images is obtained, the amount of motion (e.g., displacement) of the tissue is obtained, the strain of the tissue is measured by spatially differentiating the amount of motion, and an elastic modulus of the tissue is measured for tissue diagnosis. Further, the measured strain or the distribution of elastic moduli is displayed as an elastic image.

The elastic image, serving as the strain or the elastic modulus, is displayed as a color image added with information on the hue of red, blue, and the like, depending on the amount of strain or the elastic modulus of the tissue. That is, the tumor spread or tumor size is easily diagnosed by displaying an image that is obtained by adding, mainly, a specific color to a hard portion of the tissue. As disclosed in Patent Document 1 and Patent Document 2, the elastic images, serving as color images, are arranged on the same screen as that of a B-mode image, or are overlaid to and are displayed on the B-mode image, as mentioned above. In particular, Patent Document 2 proposes that the elastic images are displayed by varying the luminance of red, blue or another color, depending on the elastic modulus.

However, in the ultrasonic imaging apparatus disclosed in Patent Document 2, the color assignment is not considered upon setting the strain or the elastic modulus as color images. In general, in order to display a physical quantity, such as the distribution of temperatures, by varying the hue for the purpose of easy understanding, the temperature within a display range from the minimum value to the maximum value thereof is classified to a plurality of segments. The colors from red to blue via a neutral color corresponding to the segments are assigned by varying the hue in view of tone.

The elastic image is used for diagnosing the tumor, such as cancer. However, the shape and the hardness of the tumor, such as the cancer, are varied depending on individuals, portions, and medical conditions.

Therefore, the uniform fixing of the hue corresponding to the level of strain or elastic modulus necessarily causes the diagnosis of the portion size with a predetermined hardness or more. Thus, the diagnosis takes a long time, the boundary of the tumor cannot be easily identified, and there are above-mentioned problems of deterioration in convenience. In particular, there is a risk that it is impossible to accurately determine the range of the affected part to be extirpated.

Patent Document 1: JP 5-317313A
Patent Document 2: JP 2000-60853A

DISCLOSURE OF INVENTION

It is an object of the present invention to improve the convenience of use by displaying, with color segment, the level of the elasticity, such as the strain of the tissue or the elastic modulus depending on the interest of an examiner.

In order to solve the problems, according to the present invention, an ultrasonic imaging apparatus comprises: an ultrasonic probe that receives and sends ultrasonic waves from/to an object; ultrasound image structuring means that generates an ultrasound image on the basis of a reflected echo signal received by the ultrasonic probe; elastic image structuring means that obtains a physical quantity of the elasticity of the object of a region corresponding to the ultrasound image on the basis of the reflected echo signal and generates a color elastic image; display means that overlays the ultrasound image to the color elastic image, or arranges the ultrasound image and the color elastic image and displays the resultant image on a screen; and input means that variably sets a corresponding relationship between a hue of the color elastic image displayed on the screen and the level of a physical quantity.

Thus, a corresponding relationship between the hue and a physical quantity of the color elastic image is variably set via the input means on the basis of examinee determination, thereby displaying the color elastic image by adding favorite easily-viewed colors to the portions of the tissue with the elastic level, such as desired strain or elastic modulus. That is, for a diagnostic target, e.g., upon diagnosing the tumor, such as the cancer, it is possible to display the region with desired hardness to be observed with a specific color determined depending on the individual difference or medical condition. As a consequence thereof, the convenience of use such that the identification between the region to be observed and the region not to be observed becomes easy, and the diagnosis is fast can be improved.

In this case, preferably, the corresponding relationship between the physical quantity and the hue of the color elastic image set by the input means may be displayed with a color bar on the screen.

Further, in the display operation with the color bar, a large physical quantity and a small physical quantity can be displayed with different hues and the boundary between the hue having the large physical quantity and the hue having the small physical quantity can be displayed with another hue. That is, a boundary region with hardness to be observed by the examinee is displayed with different color from that of another region on the color elastic image and, therefore, a region of interest is obviously displayed and the boundary region of the tissue, such as the cancer, can be easily identified. Thus, the visibility can be improved. In this case, preferably, the boundary between the hue having the large physical quantity and the hue having the small physical quantity may be movably formed with the input means. Thus, the spread of the boundary region with hardness can be easily observed.

Furthermore, the color elastic image can be displayed alternatively a larger region or a smaller region than the setting physical quantity with a set hue. In addition, the color elastic image has a peripheral region including a setting value of the physical quantity with the hue different from the hue of another region. In this case, the hue of the peripheral region has a tone in accordance with the level of the physical quantity. Thus, only a portion with a hard region of interest or a portion with a soft region of interest can be displayed with a color image.

Specifically, the elastic image structuring means comprises: a color conversion table that is rewritable and sets a relationship between the level of the physical quantity and the color of the color elastic image; calculating means that a physical quantity of the elasticity of the object of a region corresponding to the ultrasound image on the basis of the reflected echo signal; color image generating means that reads the color corresponding to the obtained physical quantity from the conversion table and generates a color elastic image indicating the distribution of physical quantities; and input means that rewrites contents of the color conversion table. Further, the elastic image structuring means displays, on the screen, a color bar indicating a corresponding relationship between the level of the physical quantity and the hue of the color elastic image, set to the color conversion table.

BRIEF DESCRIPTION OF THE DRAWINGS

FIG. 5 is an explanatory diagram of a corresponding relationship between the distribution of elastic moduli and hue information on a color conversion table according to the second embodiment.

BEST MODE FOR CARRYING OUT THE INVENTION

Hereinbelow, a specific description is given of embodiments of the present invention with reference to the drawings.

Figure 1:
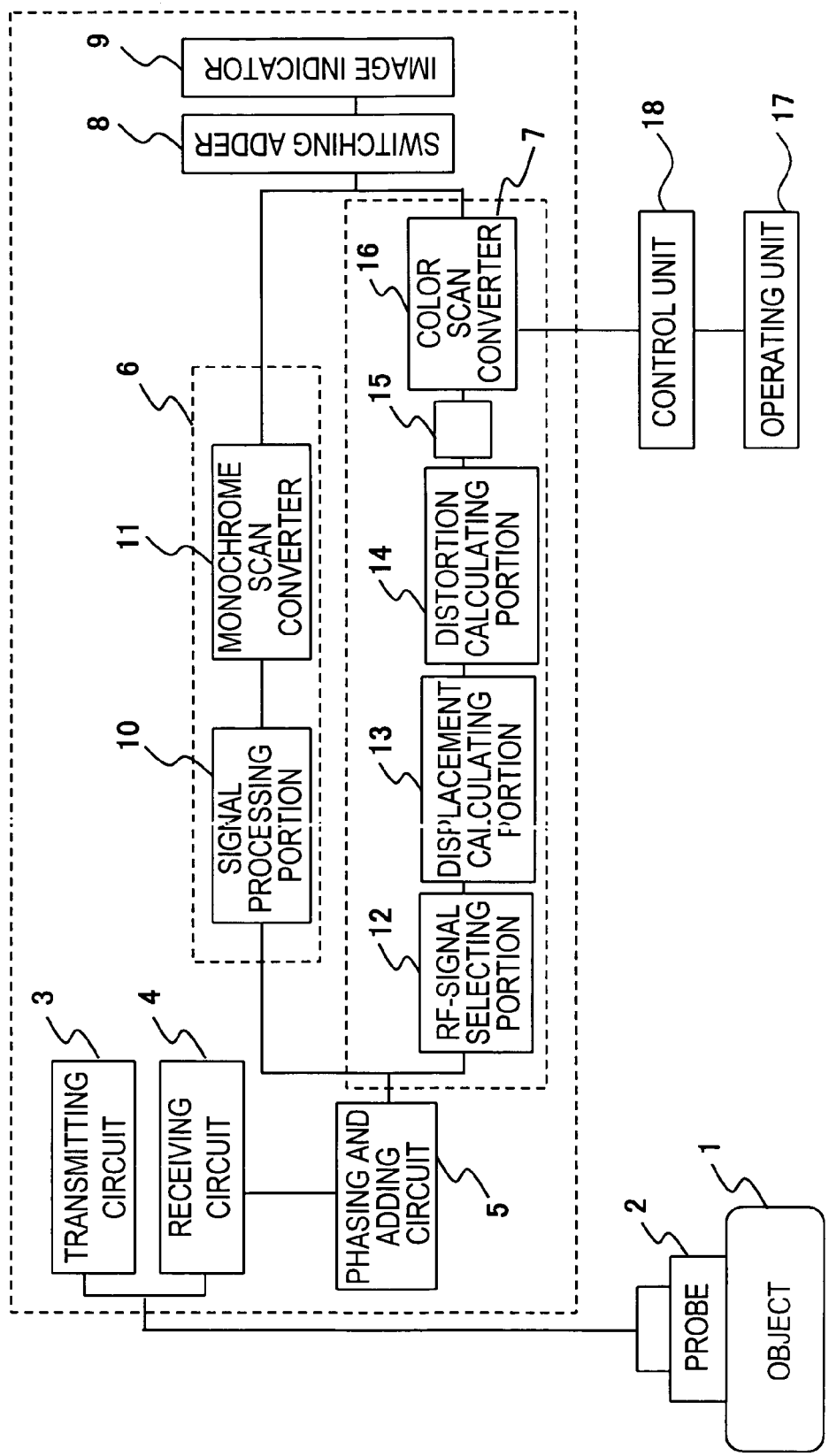
FIG. 1 is a block diagram showing the entire structure of an ultrasonic imaging apparatus according to embodiments of the present invention.

FIG. 1 is block diagram showing the structure of an ultrasonic imaging apparatus according to embodiments of the present invention. Referring to FIG. 1, according to the embodiments, an ultrasonic imaging apparatus comprises: a probe 2 that comes into contact with an object 1 and is thus used; a transmitting circuit 3 that repeatedly sends ultrasonic waves to the object 1 via the probe 2 at a predetermined time interval; a receiving circuit 4 that receives reflected echo signals on time series generated from the object 1; and a phasing and adding circuit 5 that phases and adds the received reflected echoes and generates RF signal data on time series. Further, the ultrasonic imaging apparatus comprises: an ultrasound image structuring unit 6 that structures a shading tomographic image, e.g., a monochrome tomographic image, of the object 1 on the basis of the RF signal data output from the phasing and adding circuit 5; and an elastic image structuring unit 7 that measures the displacement of the tissue of the object 1 from the RF signal data of the phasing and adding circuit 5, obtains elastic data, and structures a color elastic image. Further, the ultrasonic imaging apparatus comprises: a switching adder 8 that changes a rate between the monochrome ultrasound image and the color elastic image and synthesizes the images; and an image indicator 9 that displays the synthesized images. The ultrasonic imaging apparatus shown in FIG. 1 is properly operated by an external operator (examiner) via an operating unit 17 and a control unit 18. Note that the signals output from the phasing and adding circuit 5 can be signals I and Q for combining and demodulating RF signal frame data, e.g., RF signals.

The probe 2 comprises a plurality of vibrators, and has a function for receiving and transmitting ultrasonic waves via the vibrators to/from the object 1 with electronic beam-scanning. The transmitting circuit 3 has a function for generating transmitting pulses to generate ultrasonic waves by driving the probe 2, and for setting the convergent point of the sent ultrasonic beams with an arbitrary depth. The receiving circuit 4 generates an RF signal by amplifying, with predetermined gain, the reflected echo signals received by the probe 2. The phasing and adding circuit 5 controls the phase by inputting the RF signal amplified by the receiving circuit 4, forms ultrasonic beams converged at a plurality of convergent points, and generates the RF signal data. In general, upon measuring the elasticity of the tissue, the object 1 is pressurized, the displacement of the diagnostic portion under the pressurizing operation is measured, the strain and the elastic modulus are calculated and the elastic image is generated. In the pressurizing operation, the distribution of stress is effectively applied to the body cavity of the diagnostic portion of the object 1 while the probe 2 receives and sends the ultrasonic waves. Therefore, a pressurizing plate is uniformly attached to a receiving and transmitting surface of the ultrasonic waves of the probe 2, a pressurizing surface comprising the receiving and transmitting surface of the ultrasonic waves and the pressurizing plate of the probe 2 comes into contact with the body surface of the object, the pressurizing surface is moved up and down, and the object is pressed (pressurized and depressurized).

The ultrasound image structuring unit 6 comprises a signal processing portion 10 and a monochrome scan converter 11. Herein, the signal processing portion 10 inputs the RF signal data from the phasing and adding circuit 5 and performs signal processing, e.g., gain correction, log compression, detection, edge enhancement, and filtering processing, and obtains ultrasound image data. Further, although not shown, the ultrasound image structuring unit 6 comprises: an A/D converter that converts the ultrasound image data from the monochrome scan converter 11 and the signal processing portion 10 into a digital signal; a plurality of frame memories that store a plurality of pieces of the converted ultrasound image data on time series; and a controller. The monochrome scan converter 11 obtains, as one image, ultrasound image frame data in the object 1 stored in the frame memory, and reads the obtained ultrasound image frame data synchronously to a TV signal. That is, in order to obtain the RF signal frame data of the object including the moving tissue at an ultrasonic period with the reflected echo signals output from the signal processing portion 10 and to display the RF signal frame data, the monochrome scan converter 11 comprises ultrasound image scanning means for reading the RF signal frame data at a TV-signal period and means for controlling the system.

The elastic image structuring unit 7 comprises: an RF signal selecting portion 12; a displacement calculating portion 13; a strain calculating portion 14; an elastic data processing portion 15; and a color scan converter 16. The color scan converter 16 is connected to the operating unit 17 via the control portion 18, and can control the hue of the elastic image from the operating unit 17. Herein, the operating unit 17 comprises operating equipment, such as a keyboard, a track ball, and a mouse. Although not shown, a pressure gauge is attached to the probe 2 having a pressure measuring portion that measures a pressure (pressing force) for pressing the probe 2 to the object 1.

The RF signal selecting portion 12 comprises a frame memory and a selecting section. The RF signal selecting portion 12 stores, to the frame memory, a plurality of pieces of the RF signal data output from the phasing and adding circuit 5, and selects one set, that is, two pieces of the RF signal frame data from the stored RF signal frame data. For example, the RF signal selecting portion 12 sequentially assures, in the frame memory, the RF signal data on time series generated on the basis of a frame rate of the image by the phasing and adding circuit 5. In accordance with an instruction of the control unit 18, the RF signal frame data (N) currently-assured is selected by a selecting portion, as first data. Simultaneously, one piece of the RF signal frame data (X) is selected from the RF signal frame data (N-1, N-2, N-3, . . . , N-M) that have been assured. Herein, reference symbols N, M, and X denote index numbers which are natural numbers and are added to the RF signal frame data.

The displacement calculating portion 13 obtains the displacement of the tissue from one set of the RF signal frame data. For example, the displacement calculating portion 13 performs one-dimensional or two-dimensional correlation processing of one set of the RF signal frame data (N) and (X) selected by the RF signal selecting portion 12, and obtains the displacement or a motion vector of the tissue corresponding to the ultrasound image, that is, the distribution of one-dimensional or two-dimensional displacement on the displacement direction and the amount of displacement. Herein, a detecting method of the motion vector includes a block matching method and a gradient method disclosed in JP 5-317313A. Further, according to the block matching method, the image is divided into blocks comprising N×N pixels, attention is paid to the block within an interest region, the block that is the most approximate to the block to which the attention is paid is searched from the previous frames, and a sample value is determined on the basis of the prediction coding, that is, the difference, by referring to the searched block.

Herein, the strain data can be calculated by spatially differentiating the amount of motion of the tissue, e.g., the displacement. Further, the data on the elastic modulus can be calculated by dividing the change in pressure by the change in amount of motion. First, the strain calculating portion 14 calculates the strain data by spatially differentiating the amount of motion of the tissue, e.g., the displacement, output from the displacement calculating portion 13. Reference symbol $\Delta L$ denotes the displacement measured by the displacement calculating portion 13, and reference symbol $\Delta P$ denotes a pressure measured by the pressure measuring portion (not shown). Since strain S can be calculated by spatially differentiating $\Delta L$, the strain S is obtained by an expression of $S=\Delta L/\Delta X$. Herein, the pressure applied to the body surface can be directly measured by a pressure sensor existing between the body surface and the contact surface of a pressurizing mechanism, or can be measured by a method disclosed in Japanese Patent Application No. 2003-300325 filed by the present application of the present invention. Further, Young's modulus Ym of the elastic modulus data is calculated by an expression of $Ym=(\Delta P)/(\Delta L/L)$. Since the elastic modulus of the tissue corresponding to the point on the ultrasound image can be obtained from the Young's modulus, the two-dimensional elastic image data can be continuously obtained. Note that the Young's modulus is the ratio of a simple strain applied to a substance to a strain caused in generated in parallel with the strain. Note that the strain calculating portion 14 may perform various image processing of the calculated elastic frame data, including smoothing processing on the coordinate plane and contrast optimizing processing, and smoothing processing in the time-base direction between the frames, and may output the elastic frame data after the processing, as the amount of strain.

The elastic data processing portion 15 comprises a frame memory and an image processing section, assures the elastic frame data output on time series from the strain calculating portion 14 to the frame memory, and performs the image processing of the assured frame data with the image processing section in accordance with an instruction of the control unit 18.

The color scan converter 16 converts the elastic frame data from the elastic data processing portion 15 into hue information in accordance with a color conversion table, which will be described later. That is, the color scan converter 16 converts the elastic frame data into the hue information comprising three primary colors of light, i.e., color codes of R (Red), G (Green), and B (Blue). For example, the color scan converter 16 converts the elastic data with large strain into the red code and simultaneously converts the elastic data with small strain into the blue code. Note that the tones of R, G, and B are assigned to 256 steps, and a tone "256" means the display operation with large luminance and, on the other hand, a tone "0" means that the image is not displayed.

The switching adder 8 comprises: a frame memory; an image processing section; and an image selecting section. Herein, the frame memory stores ultrasound image data from the monochrome scan converter 11 and elastic image data from the color scan converter 16. The image processing section adds and synthesizes the ultrasound image data and the elastic image data assured in the frame memory with a setting ratio in accordance with an instruction from the control unit 18. Luminance information and hue information of the pixels of the synthesized image is obtained by adding information on the monochrome ultrasound image and information on the color elastic image with the setting ratio. Further, the image selection section selects an image to be displayed on the image indicator 9 from the ultrasound image data and the elastic image data in the frame memory and the synthesized image data in the image processing section in accordance with an instruction from the control unit 18. Note that the ultrasound image and the elastic image may be individually displayed without synthesis.

Next, a description is given of the operation of the ultrasonic imaging apparatus with the above-mentioned structure. In the ultrasonic imaging apparatus 1, the transmitting circuit 3 repeatedly sends ultrasonic waves to the object 1 via the probe 2 that comes into contact with the object 1 at the time interval, the receiving circuit 4 receives the reflected echo signals on time series generated from the object 1, and the RF signal data is generated by phasing and addition. The ultrasound image structuring unit 6 generates a shading tomographic image, e.g., a monochrome B-mode image on the basis of the RF signal data. In this case, the scanning operation in a predetermined direction is performed with the probe 2, thereby obtaining one ultrasound image. The elastic image structuring unit 7 generates a color elastic image on the basis of the RF signal data that is phased and added by the phasing and adding circuit 5. The switching adder 8 adds the obtained monochrome ultrasound image and the color elastic image and generates the synthesized image thereof.

Herein, a description is given of an example of processing of the switching adder 8 according to the embodiments. Hereinbelow, the ultrasound image data input to the ultrasound image structuring unit 6 is ultrasound image data i, j and ultrasound image data input to the elastic image structuring unit 7 is elastic image data i,j. Subscripts i and j denote coordinates of data components. As mentioned above, the ultrasound image data and the elastic image data include the luminance information and the coordinate information, corresponding to the image display operation.

First, the ultrasound image data having monochrome luminance information is converted into the hue information. When the ultrasound image data after conversion has the same bit length as that of the monochrome luminance information, hue data of the converted ultrasound image data, i.e., three primary-color (R, G, B) data of light can be expressed by the following Expression 1.

(Ultrasound image data $R$)$i,j$=(Ultrasound image data)$i,j$  (Expression 1)

(Ultrasound image data $G$)$i,j$=(Ultrasound image data)$i,j$ (Ultrasound image data $B$)$i,j$=(Ultrasound image data)$i,j$ Subsequently, the converted ultrasound image data and the elastic image data are added with a setting ratio $\alpha$ for synthesis. Herein, the setting ratio $\alpha$ is arbitrarily set in advance in accordance with the characteristic of the tissue and a relationship of $1<\alpha<1$ is established. With the setting ratio $\alpha$, the synthesized image is generated as shown by the following Expression 2. The synthesized image is arbitrarily selected and is displayed on the image indicator 9.

(Synthesized data $R$)$i,j$=$(1-\alpha)\times$(ultrasound image data $R$)$i,j$+$\alpha X$(elastic image data $R$)$i,j$  (Expression 2)

Figure 3:
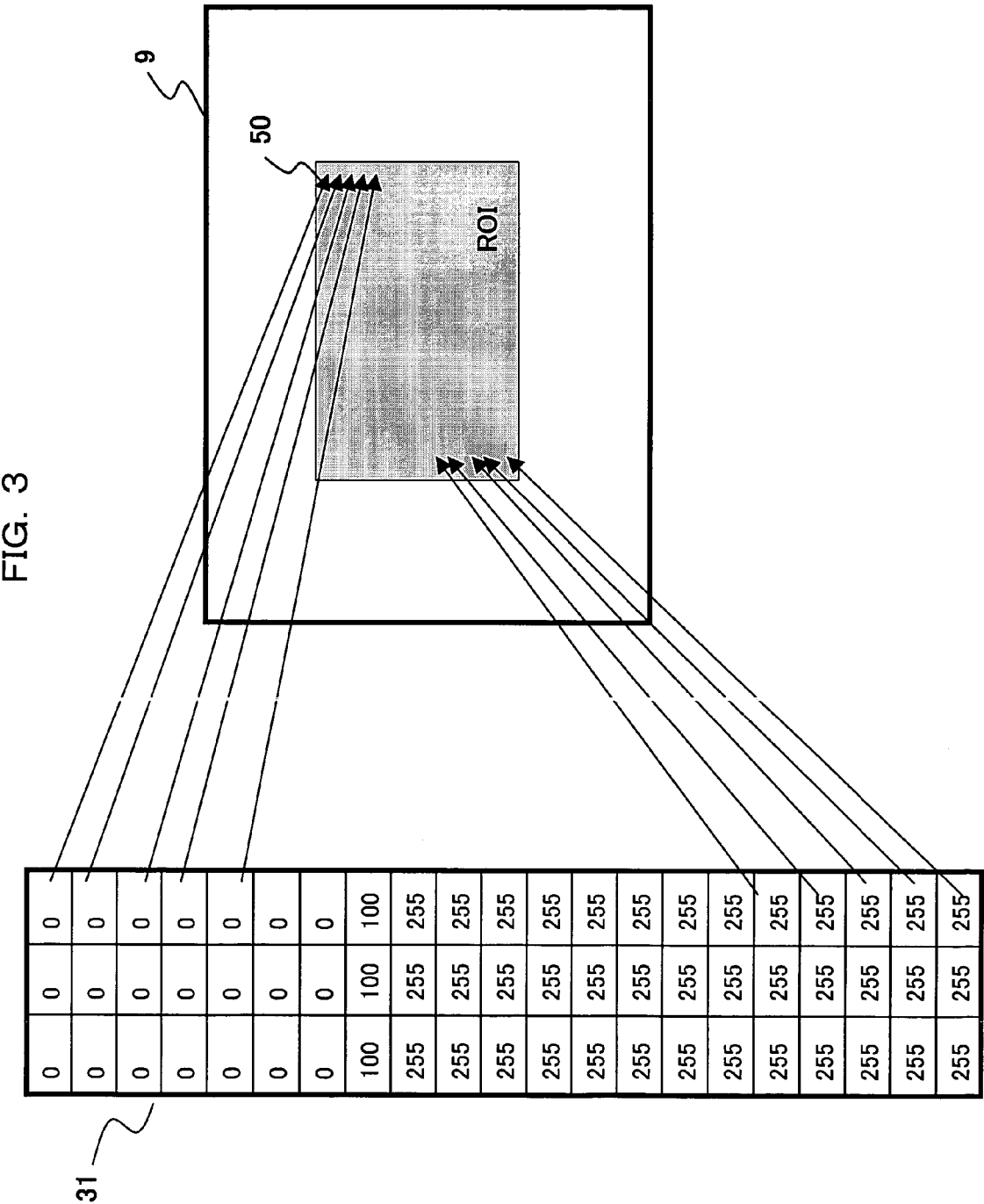
FIG. 3 is a diagram showing an example of a display image.

(Synthesized data $G$)$i,j$=$(1-\alpha)\times$(ultrasound image data $G$)$i,j$+$\alpha X$(elastic image data $G$)$i,j$ (Synthesized data $B$)$i,j$=$(1-\alpha)\times$(ultrasound image data $B$)$i,j$+$\alpha X$(elastic image data $B$)$i,j$ A description is given of the above-synthesized image with reference to FIG. 3. FIG. 3 is a diagram showing a display example of the ultrasound image, the elastic image, and the synthesized image according to the embodiments. An image obtained by superimposing the color elastic image to the monochrome ultrasound image is displayed, and an image obtained by synthesizing the monochrome ultrasound image and the color elastic image by the switching adder 8 is displayed.

Upon obtaining the elastic image, a region of interest (ROI) 50 for determining a range for obtaining the elastic image on the monochrome ultrasound image is set, and the elastic image of the ROI 50 is obtained. The ROI 50 is set because a region for obtaining the elastic image is limited to the depth direction and even when a wide region is obtained, the possibility of a large part of regions having noise is high. The ROI 50 can be arbitrarily set mainly in the pressing direction of the probe to the object in accordance with an instruction from the operating unit 17.

Figure 2:
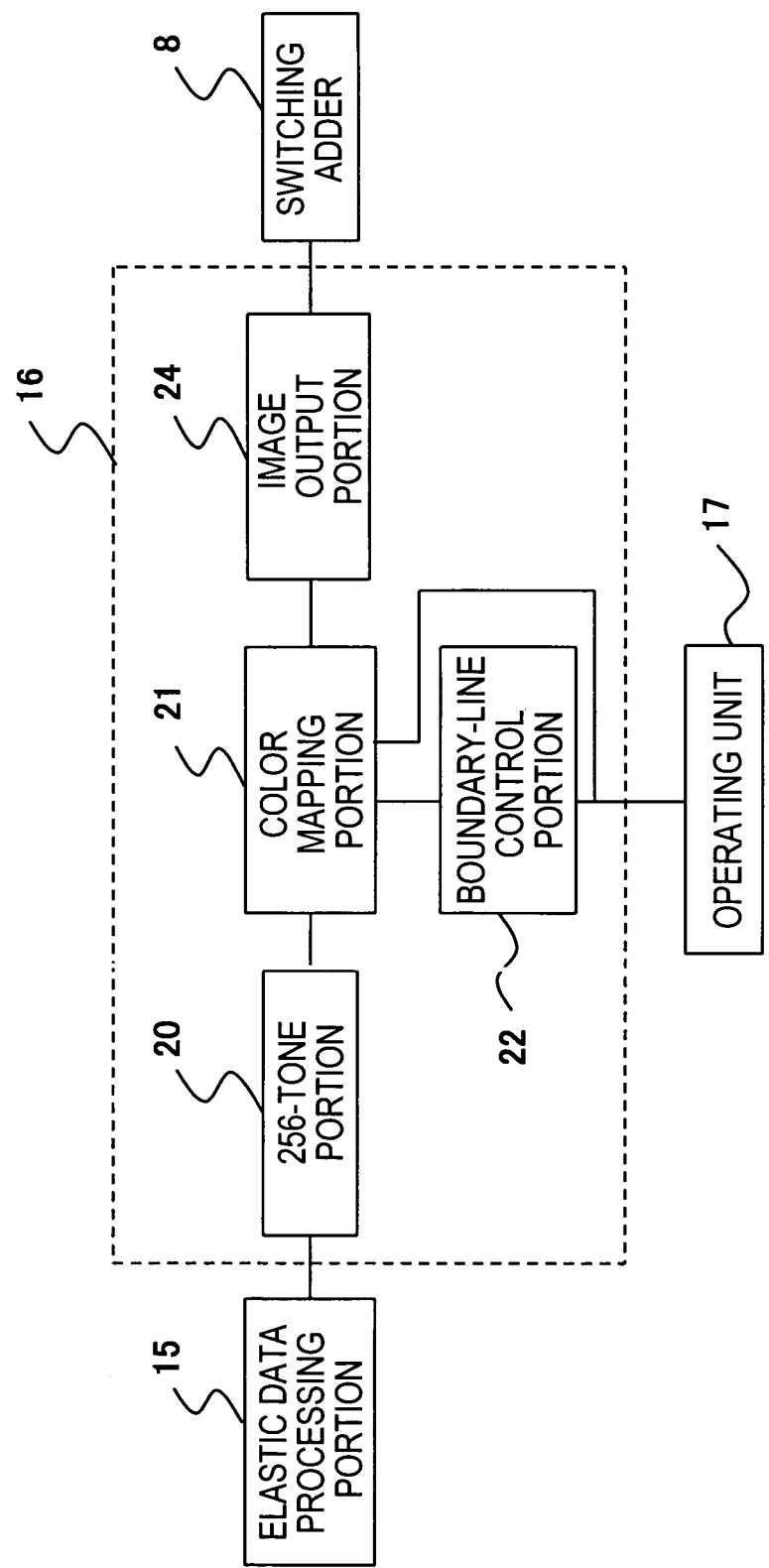
FIG. 2 is a diagram showing the detailed structure of a feature according to the present invention.

Herein, a detailed description is given of portions, serving as the feature according to the present invention with reference to FIG. 2. The color scan converter 16 outputs, to the switching adder 8, strain data output from the elastic image data processing unit or the data on the elastic modulus, as the elastic image data including the information on the converted three primary colors. Referring to FIG. 2, the color scan converter 16 comprises, as the detailed structure: a 256-tone portion 20 that assigns the data to three primary colors on the basis of the strain data or the data on the elastic modulus; a boundary line control portion 22 that switches a color range and changes a boundary portion in accordance with an instruction from the operating unit 17; a color mapping portion 21 that creates a color map matching the image from the 256-tone portion 20 and the boundary line control portion 22; and an image data output portion 24 that outputs the image data from the color mapping portion 21 to the switching adder 8. In order to assign the elastic frame data, i.e., the amount of strain, corresponding to the pixel output from the elastic data processing portion 15 to 256 tones, the 256-tone portion 20 sets the data to a signal with the structure of 8 bits under a matching rule, and outputs the tone data of (256 tones) with the structure of 8 bits to the color mapping portion 21. The color mapping portion 21 inputs the tone data of (256 tones) with the structure of 8 bits output from the 256-tone portion 20, and adds the hue information of red, green, and blue to the tone data in accordance with the color conversion table corresponding to color bars that are preset.

Next, a description is given of the color scan converter that displays the color elastic image according to the embodiments.

First Embodiment

Figure 4:
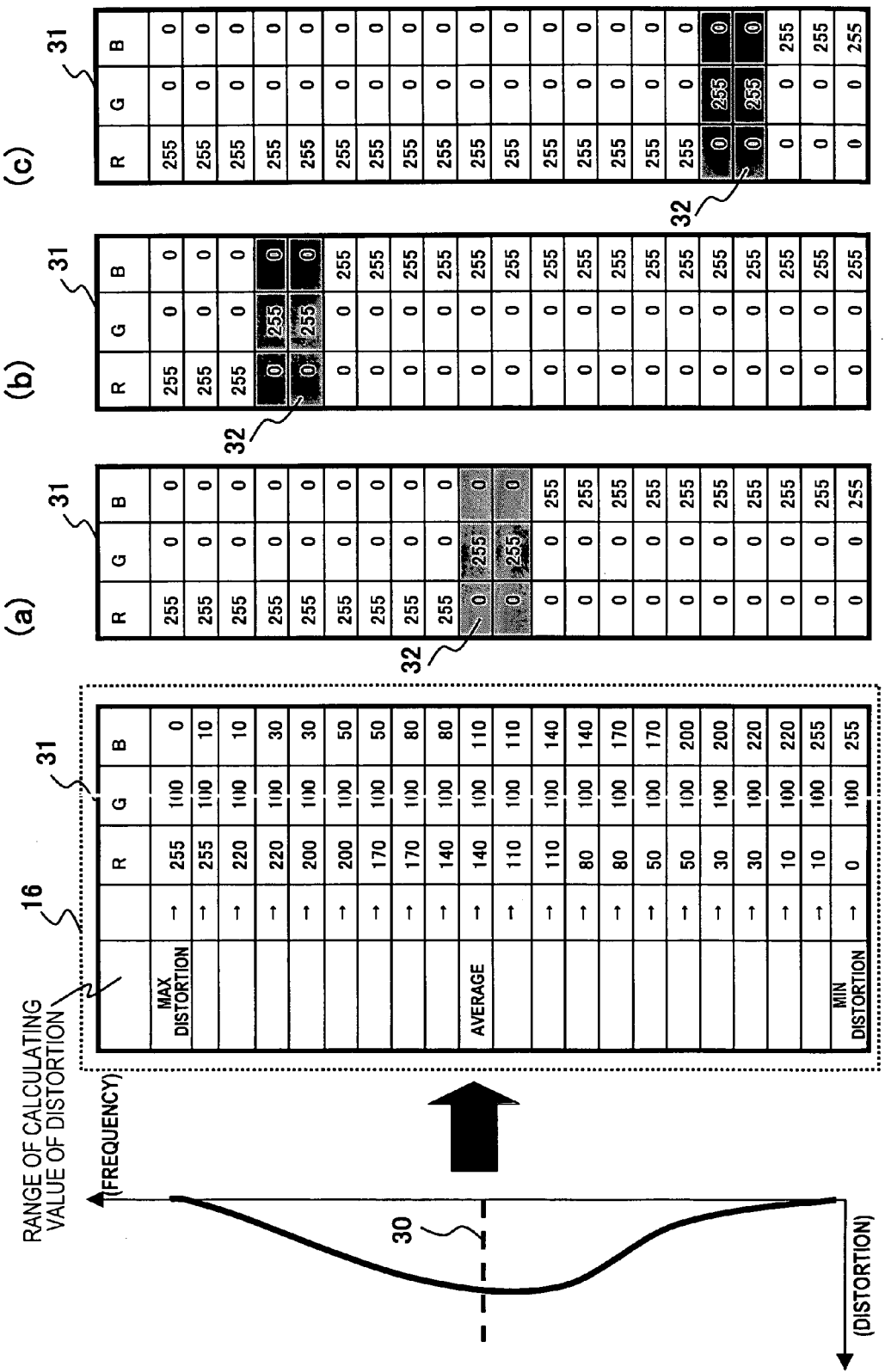
FIG. 4 is an explanatory diagram of a corresponding relationship between the distribution of strains and hue information on a color conversion table according to the first embodiment.

According to the first embodiment, a case of displaying the strain with colors will be described. First, the strain data S is obtained every frame on the basis of S=$\Delta L/\Delta X$, and statistical processing of the strain in the ROI 50 is performed. FIG. 4 is a graph with the abscissa, serving as frequency, and the ordinate, serving as strain and, in the statistical processing, the strains corresponding to strains in the ROI 50 are distributed on the graph shown in FIG. 4, the strains are added, and the total amount of strains is calculated. An average 30 of the strains is calculated by calculation of (the total amount of strain)/(the number of pixels). Colors are assigned in accordance with the fractions from a maximum strain value to a minimum strain value based on the average 30 of the strains. Specifically, the hue information comprising color codes of red (R), green (G), and blue (B) is assigned to table coordinates corresponding to strain values of the color conversion table 31 of the hue information stored in the memory provided for the color scan converter 16.

In the case of assigning the colors, upon displaying a soft region with a large strain with red, the red R color code, to be assigned to the coordinate corresponding to the region with large strain in the color conversion table 31 shown in FIG. 4($a$), is set to be large. The green G and blue B are set to be small. Thus, the elastic image data is generated on the basis of the color conversion table 31, thereby displaying the soft region with red. On the other hand, upon displaying a hard region with small strain with blue, the blue B color code, to be assigned to the coordinate corresponding to the region with small strain in the color conversion table 31, is set to be large. The green G and red R are set to be small.

Figure 6:
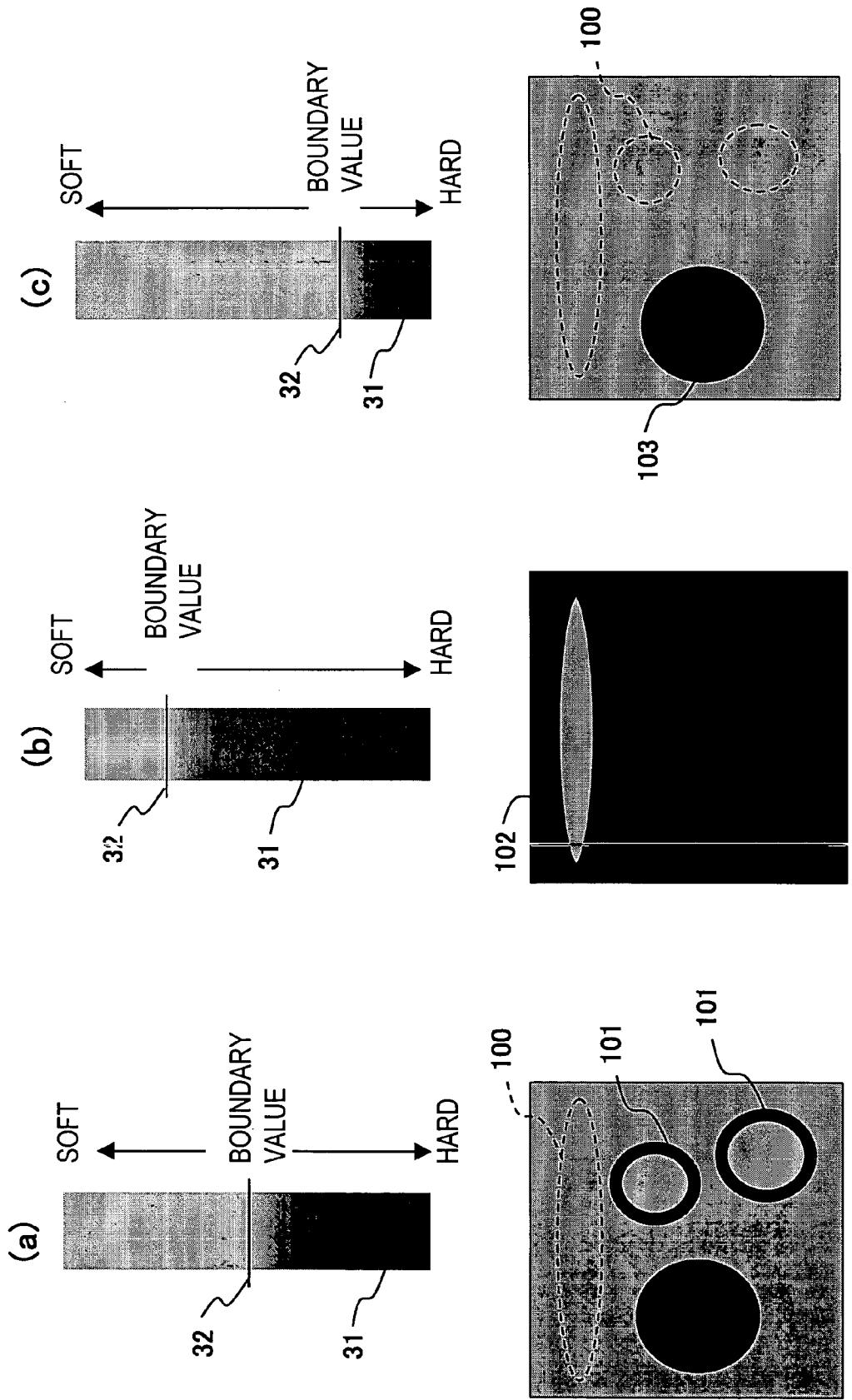
FIG. 6 is a diagram showing examples of image display operation according to the first and second embodiments.
Figure 7:
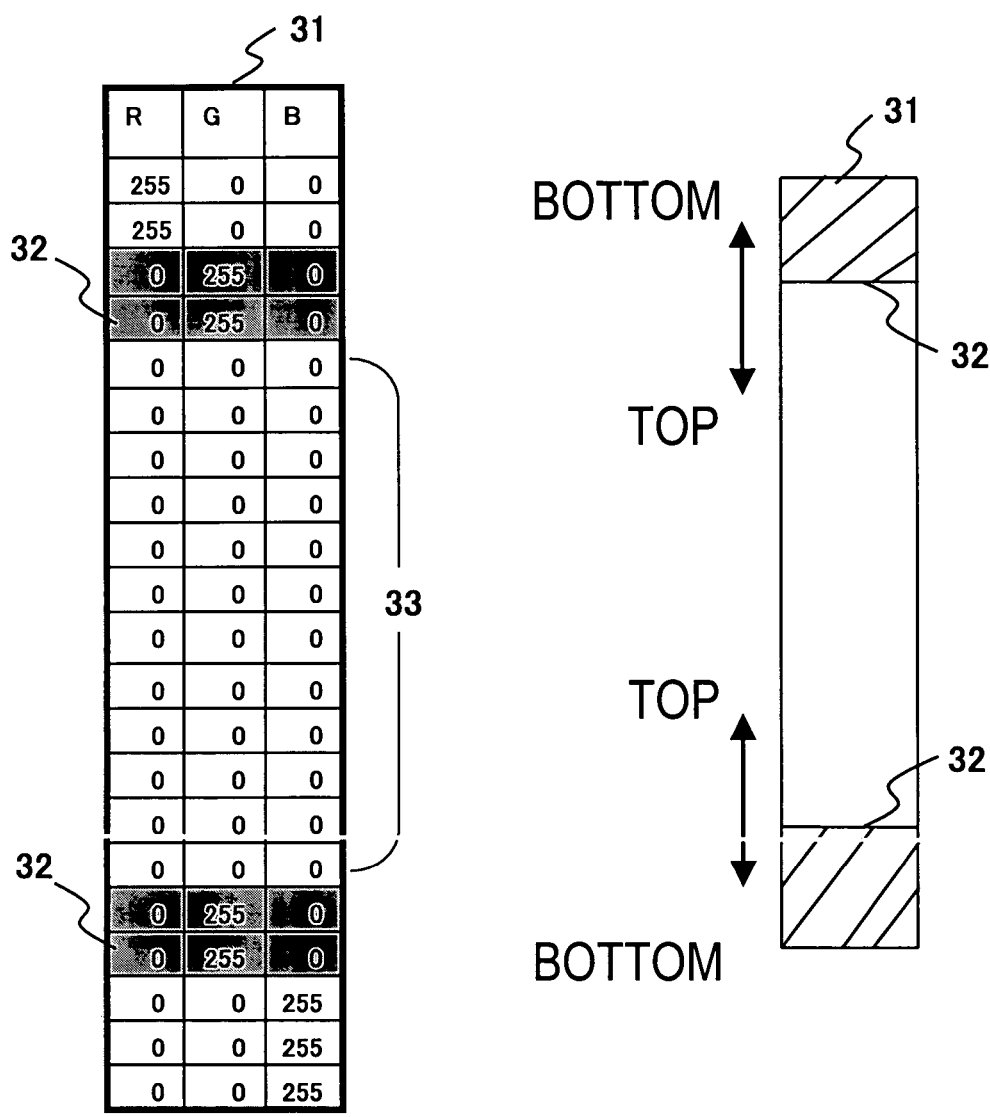
FIG. 7 is an explanatory diagram of the correspondence between hue information on a color conversion table and the display operation with color bars according to the third embodiment.

When a hard region widely exists in the ROI 50 and the hard region is entirely to be grasped, the color codes are set for clear display operation by extending the range of blue B in the assignment of red R, green G, and blue B relative to the strain values in the color conversion table 31 shown in FIG. 4. Further, in order to clearly display the boundary portion 32 between the hard region and the soft region, an instruction is input to the boundary line control portion 22 form the operating unit 17, thereby setting the boundary portion 32 between the red R and blue B to green G. Furthermore, in order to display the hard region with blue B and the soft region with red R on the basis of the average 30 of the strain as center, the hue information in the color conversion table 31 is assigned. The elastic image data is generated and is displayed on the basis of the assignment. Thus, referring to FIG. 6(a), it is possible to widely identify where the hard tissue exists. Note that a broken line 100 shown in FIG. 6 is not displayed on the elastic image and is used to describe a corresponding relationship among FIGS. 6(a), (b), and (c). Further, reference symbol 102 denotes the soft region, reference symbol 103 denotes the hard region, and reference symbol 101 denotes a region with an average hardness.

On the other hand, when the soft region exists in the ROI 50 and the soft region is entirely to be grasped, in order to clearly display the red R, the red R, green G, and blue B are assigned to the coordinates corresponding to the region with small strain in the color conversion table 31 shown in FIG. 4. In order to clearly display the boundary portion 32 between the hard region and the soft region, an instruction is input to the boundary line control portion 22 from the operating unit 17, and the boundary portion 32 between the red R and the blue B is set to the green G. The color conversion table 31 is set by narrowing a display range of red R so as to display the soft range with red R and widely display the blue B. The elastic image data is generated and is displayed on the basis of the assignment, thereby widely displaying the blue B as shown in FIG. 6(b) and using the blue B, as the background of the red R. Thus, the red R to be extracted can be obviously displayed and it is possible to easily identify where the soft tissue exists.

Further, when the hard region exists in the ROI 50 and is to be grasped, referring to FIG. 4(c), the red R, the green G, and the blue B are variably assigned to the strain in the color conversion table 31 so that blue B is obviously displayed. First, in order to clearly display the boundary portion 32 between the hard region and the soft region, an instruction is input to the boundary line control portion 22 form the operating unit 17, and the boundary portion 32 between the red R and the blue B is set. Further, the color conversion table 31 is set by narrowing a display range of the blue B and widely display the red R so as to display the hard region with the blue B. The elastic image data is generated and is displayed on the basis of the assignment, thereby widely displaying the red R as shown in FIG. 6(c) and using the red R, as the background of the blue B. The blue B to be extracted can be obviously displayed and it is possible to easily identify where the hard region exists.

As mentioned above, according to the first embodiment, the region with strain to be extracted can be obviously displayed by moving the boundary portion 32 between one soft region and the other hard region sandwiched by the boundary portion 32.

Second Embodiment

According to the second embodiment, a description is given of the case of displaying the elastic modulus with colors. Unlike the first embodiment, the elastic modulus is assigned, in place of the strain. The elastic modulus (Young's modulus) Ym is calculated by the expression of Ym=(ΔP)/(ΔL/L). Referring to FIG. 5, in the color conversion table 31 provided for the color converter 16, the range of calculating values of the elastic modulus is divided into a plurality of sections, and the color codes of red R, green G, and blue B are set to the sections. The hue information corresponding to the calculating value of the elastic modulus to be input is read from the color conversion table 31 and the elastic image data is generated.

Herein, when the elastic modulus is widely identified in the ROI 50, referring to FIG. 5(a), an instruction is input to the boundary line control unit 22 from the operating unit 17, similarly to the first embodiment. Further, the boundary portion 32 between the red R and the blue B is set to green G. Furthermore, the color conversion table 31 is set so as to display the region with low elastic modulus with the blue B and the region with high elastic modulus with the red R on the basis of the average value of the elastic modulus as center. The elastic image data is generated and is displayed on the basis of the assignment. With the display operation, it is possible to widely identify where the region with high elastic modulus or low one exists.

When the region with high elastic modulus is to be identified in the ROI 50, referring to FIG. 5(b), an instruction is input to the boundary line control portion 22 from the operating unit 17 similarly to the first embodiment, and the boundary portion 32 between the red R and the blue B is set to the green G. Further, the color conversion table 31 is set so that the region with low elastic modulus is displayed with the blue B and the region with high elastic modulus is displayed with the red R on the basis of the region with high elastic modulus as center. The elastic image data is generated and is displayed on the basis of the assignment. With the display operation, it is possible to identify where the tissue with high elastic modulus exists.

Further, when the region with low elastic modulus is to be identified in the ROI 50, referring to FIG. 5(c), an instruction is input to the boundary line control portion 22 from the operating unit 17 similarly to the first embodiment, and the boundary portion 32 between the red R and the blue B is set to the green G. Further, the color conversion table 31 is set so that the region with low elastic modulus is displayed with the blue B and the region with high elastic modulus is displayed with the red R on the basis of the region with low elastic modulus as center. The elastic image data is generated and is displayed on the basis of the assignment. With the display operation, it is possible to identify where the tissue with low elastic modulus exists.

As mentioned above, according to the second embodiment, the region to be extracted with elastic modulus can be obviously displayed by moving the boundary portion 32 between one region with high elastic modulus and the other region with low elastic modulus sandwiched by the boundary portion 32.

Third Embodiment

According to the third embodiment, a description is given of the case of displaying only a desired region with strain or elastic modulus. Unlike the first and second embodiments, the assignment of the hue information in the color conversion table 31 is changed so as to prevent the display operation of a neutral portion 33. An instruction is input to the boundary line control portion 22 from the operating unit 17 and the hue information in the color conversion table 31 is changed, thereby extracting only a hard region and a soft region with desired strain and only a region with high elastic modulus and a region with low elastic modulus. As mentioned above, non-display operation of the neutral portion enables data without needing the elastic image to be removed and further enables the elastic image to be displayed with the removal of noise in the unnecessary data. Note that the boundary portion 32 may be arbitrarily moved in the vertical direction by operating the operating unit 17 or the display range may be widened. Further, it is possible to display one of the hard region and the soft region with strain or to display one of the region with high elastic modulus and the region with low elastic modulus.

According to the first to third embodiments, the soft region is displayed with the red R and the hard region is displayed with the blue B on the basis of the amount of strain. However, it is obvious that the region may be displayed with any color, irrespective of the above colors. This can be applied to the elastic modulus. Specifically, the 256-tone portion 20 may arbitrarily set the shading of color or may replace the shading of scale with a complex color obtained by combining red R, green G, and blue B. e.g., black, yellow, or pink, thereby displaying a color for easily identifying the soft region or the hard region by an examiner.

Similarly, the boundary portion 32 may be displayed by replacing the above colors including the green G with a neutral color of the red R and the blue B or a complex color obtained by combining the red R and the green G. Further, when the color of the hard region is different from that of the soft region, the boundary is clear. Therefore, an instruction may be inputted to the boundary line control portion 22 from the control unit 17 to control the switching operation f colors without displaying the boundary portion 32.

Fourth Embodiment

Figure 8:
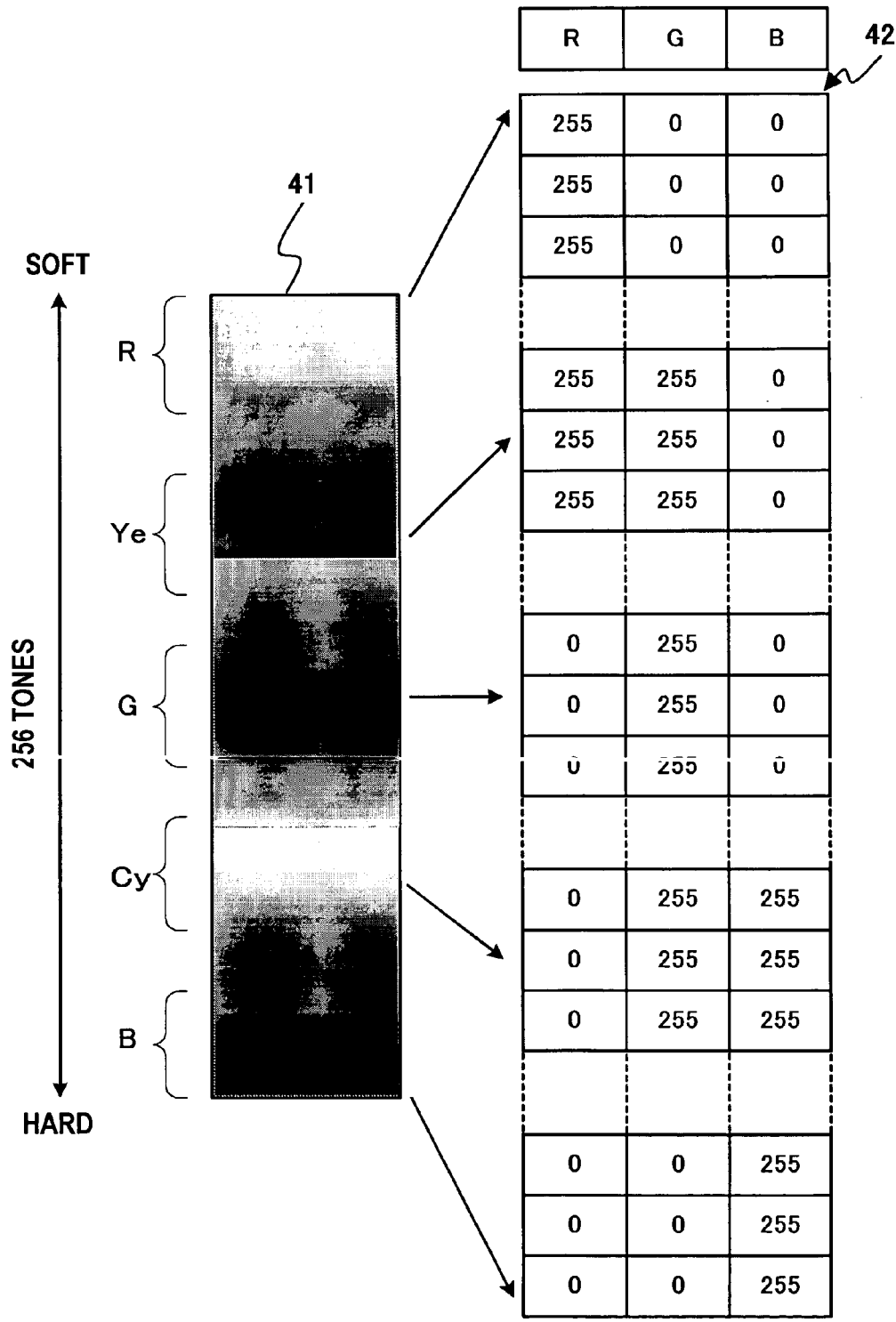
FIG. 8 is an explanatory diagram of a corresponding relationship between a color bar and hue information on a color conversion table according to the fourth embodiment.

FIG. 8 shows a color bar 41 indicating a relationship between the tone data and the hue information according to the fourth embodiment and a color conversion table 42 of the hue information corresponding to the color bar 41. Unlike the first to third embodiments, in place of the display operation of the level of the strain or the elastic module with the two colors including the red R and the blue B, the coloring operation is performed with three colors of red R, green G, and blue B. Further, according to the fourth embodiment, the boundary portion with the level of the strain or the level of the elastic modulus is not displayed.

That is, referring to FIG. 8, in the tone data in the color conversion table 42, the hue information is assigned so as to convert the soft region with the measured large strain into to the color code of the red R, the hue information is assigned so as to convert the hard region with the measured small strain into the color code of the blue B, and the hue information is assigned so as to convert the region with middle strain into the color code of the green G. Therefore, the interval between the color codes of the red R and the green G is converted into Ye (Yellow), the interval between the color codes of the green G and the blue B is converted into Cy (Cyanogen), and the hue stepwise changes at the boundary portion between the colors. However, the color conversion table shown in FIG. 8 shows only typical color codes of the color bar 41. Therefore, actually, the color code is assigned to be stepwise changed at the boundary portion of colors.

The switching adder 8 inputs the monochrome ultrasound image data from the monochrome scan converter 11 and the color elastic image data from the color scan converter 16, and adds or switches both the images. Herein, the switching adder 8 outputs only the monochrome ultrasound image data or the color elastic image data, or outputs resultant image data obtained by adding and synthesizing both the image data, that is, can variously switch the output operation. According to the fourth embodiment, upon adding and synthesizing both the image data, the switching adder 8 can overlay the color elastic image data to the monochrome B-mode ultrasound image data with predetermined transparency and can display the resultant image data on the image display 9.

Figure 9:
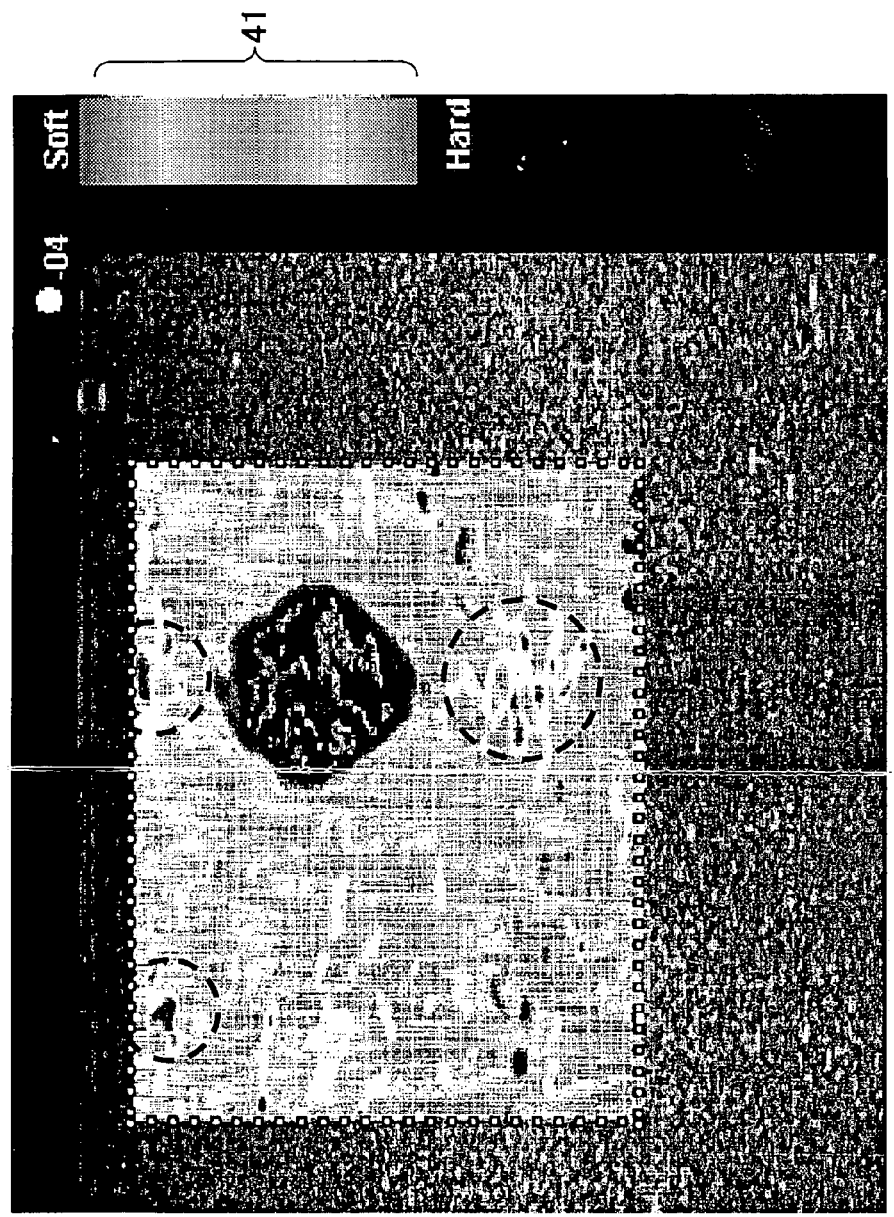
FIG. 9 is a diagram showing examples of image display operation according to the fourth embodiment.

FIG. 9 is a diagram showing a display example of the image indicator 9 in the ultrasonic imaging apparatus according to the fourth embodiment. Referring to FIG. 9, an elastic image with transparency "0" is displayed. As shown in FIG. 9, a rectangular gray region (gray region lighter than the periphery) displayed around the center of the display image is the region ROI of interest. A circular dark gray region in the rectangular interest region is the hard region, as the tissue. The light gray region other than the dark gray region is a relatively soft region. The rectangular interest region is actually displayed with a color. Since the rectangular interest region is displayed with monochrome colors in FIG. 9, the identification is not easy. However, the light gray region in the interest region is green, and the circular dark gray region is entirely blue. Note that the dark gray region in a region surrounded by a dotted circle is red and a region except for the above-mentioned dark gray region is blue in FIG. 9. In these cases, the red indicates the soft region of the tissue, the blue indicates the hard region, and the green indicates a region with middle hardness between the hard region and the soft region.

As mentioned above, the hardness of the tissue can be easily viewed by displaying the strain elastic image in the interest region with the colors in accordance with the hardness of the region. In particular, according to the fourth embodiment, it is possible to arbitrarily change the hue information of the color conversion table 42 in the color mapping portion 20 in the color scan converter 16 via the operating unit 17. Therefore, the examiner varies the hue information in the color conversion table 42 for the purpose of the diagnosis, thereby adjusting the coloring operation so as to display a region with predetermined hardness or more with the blue. As a consequence thereof, the visibility is improved and the convenience of use is further improved.

Conventionally, the hue information in the color conversion table 42 is uniformly fixed in accordance with the level of the strain or the elastic modulus. Therefore, upon diagnosing the size of a region with predetermined hardness or more or upon diagnosing the spread thereof, the region with predetermined hardness or more cannot be intuitively determined. On the contrary, according to the fourth embodiment, since the examiner can freely change the hue information in the color conversion table 42, the region with predetermined hardness or more or the spread thereof can be easily diagnosed.

Further, referring to FIG. 9, the right side of the elastic image displays the color bar 41 indicating the hardness of the elastic image. The color bar 41 is the same as that shown in FIG. 8. Although the color bar 41 is displayed with monochrome colors, the color bar 41 is actually displayed with colors in accordance with the hue information shown in the color conversion table 42 in FIG. 8 on the display screen. On the top and bottom of the color bar 41, characters "Soft" and "Hard" are displayed so as to easily identify the assignment of color and hardness. This display operation is performed because the color bar 41 corresponds to the level of strain, that is, the hardness and softness of the tissue. Therefore, when the color bar 41 corresponds to the amount of displacement, a character indicating the distance is displayed. Further, when the color bar 41 corresponds to the elastic modulus, a character indicating the unit of elastic modulus is displayed. Thus, the assignment relationship can be easily identified.

Fifth Embodiment

Figure 10:
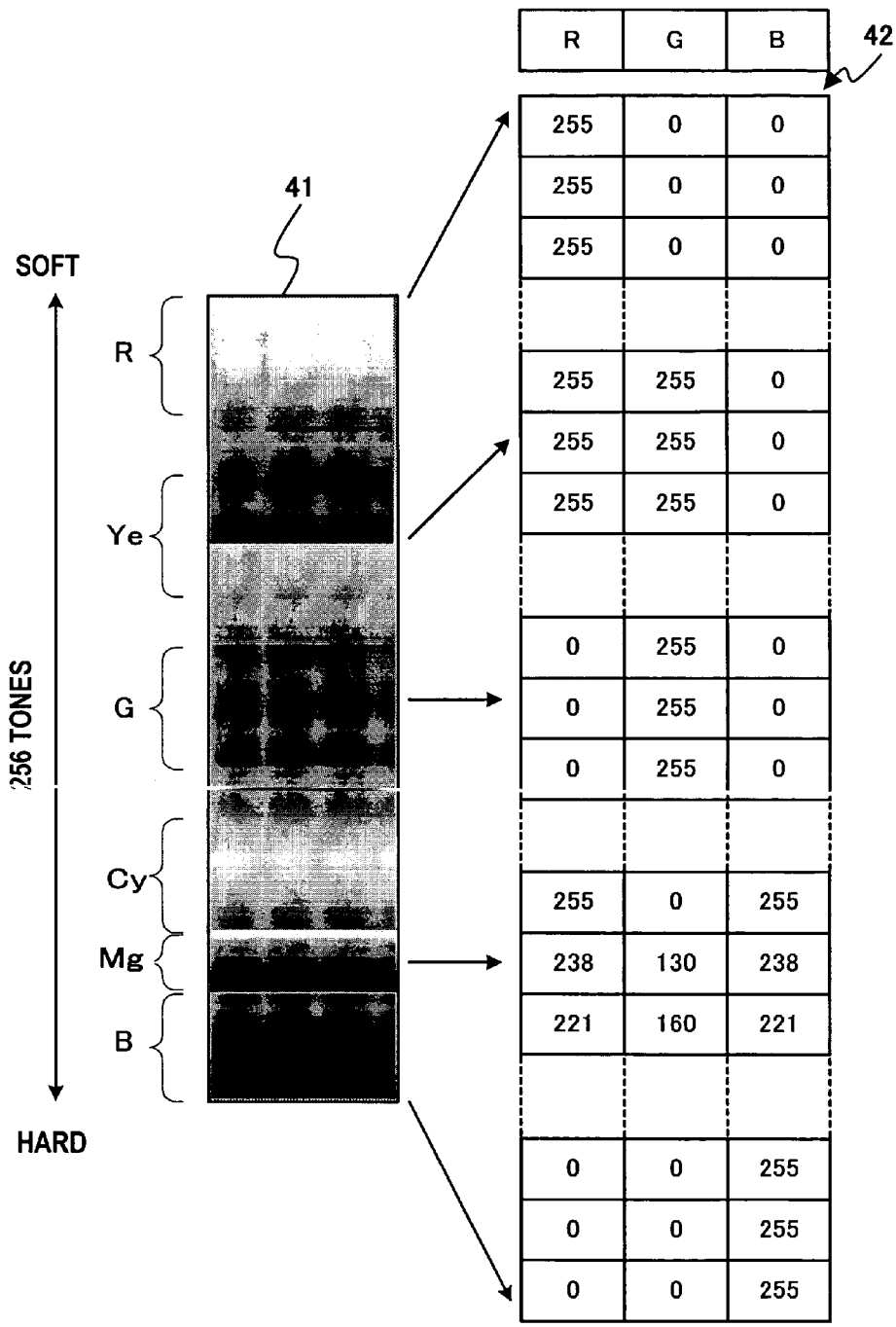
FIG. 10 is an explanatory diagram of a corresponding relationship between a color bar and hue information on a color conversion table according to the fifth embodiment.

FIG. 10 shows a color bar and a color conversion table according to the fifth embodiment. The color bar 41 according to the fifth embodiment is an example of setting the hue information so as to specifically observe the boundary of the hard region. That is, FIG. 10 shows an example in which a hue with a tone, different from peripheral hues with tones, is set to the intermediate region between a color code of the blue B and a color code of the cyan Cy in FIG. 8, serving as the boundary portion of the hard region, thereby easily identifying the intermediate region. Further, the hue at the intermediate region can stepwise be changed. Referring to FIG. 10, Mg (Magenta) color is assigned to a region of the hue which stepwise changes. The hue information of the color bar 41 is set by assigning color codes (R, G, B) in the color conversion table 42 via the operating unit 17. As shown in FIG. 10, color codes, e.g., Magenta: (255, 0, 255), Violet (238, 130, 238), and Plum (221, 160, 221) for stepwise changing the colors are assigned so that the color code of Magenta Mg stepwise change. Similarly to that shown in FIG. 8, the color bar 41 has the hue that stepwise changes near the boundary of the colors. However, referring to FIG. 10, the color conversion table 42 indicated right-adjacent to the color bar 41 shows only typical color codes. Therefore, the color codes that stepwise change are assigned near the boundary of the colors.

Sixth Embodiment

The example is given of assigning the color codes that stepwise change near the boundary of the colors according to the fifth embodiment. However, the present invention is not limited to this. That is, according to the sixth embodiment, referring to FIG. 11, a region with desired hardness is over-colored with a color code of Pink so as to emphasize only a region with interest hardness (or softness). Further, only the elastic image of the over-colored region is displayed with a pink color. The hue information is set by assigning the color codes (R, G, B) in the color conversion table 42 via the operating unit 17.

Figure 11:
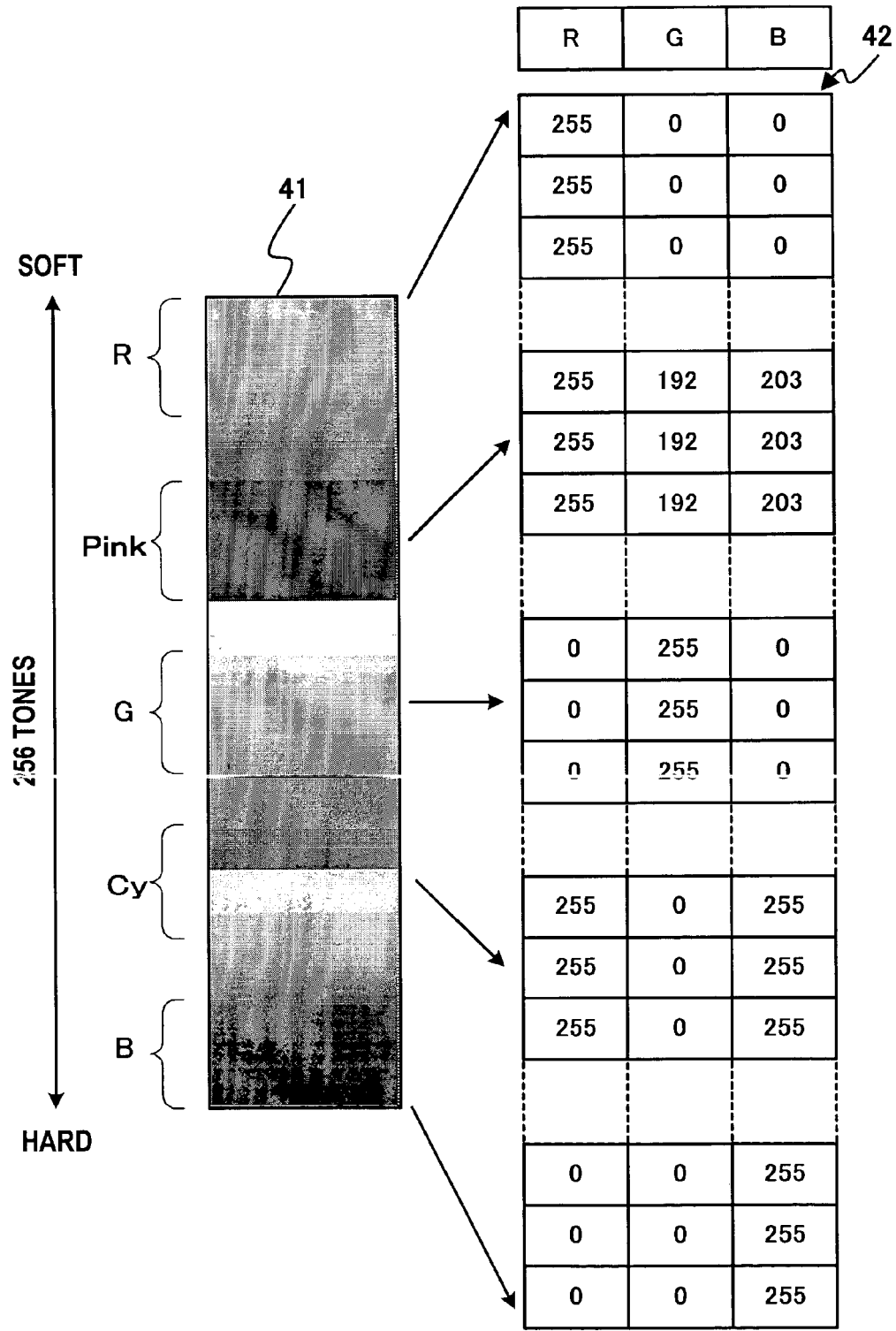
FIG. 11 is an explanatory diagram of a corresponding relationship between a color bar and hue information on a color conversion table according to the sixth embodiment.

Herein, the over-colored region of the color code according to the fifth or sixth embodiment as shown in FIG. 10 or 11 can be freely expanded and can be freely moved, and can be freely set with colors by inputting an instruction to the boundary line control portion 22 from the operating unit 17 and varying the color conversion table 42. Thus, it is possible to display, with favorite colors, the region with desired hardness to be specifically observed, or to stepwise display the region with colors. Thus, the visibility is improved. Note that the number of a region that partly has different colors is one or plural.

Seventh Embodiment

Figure 12:
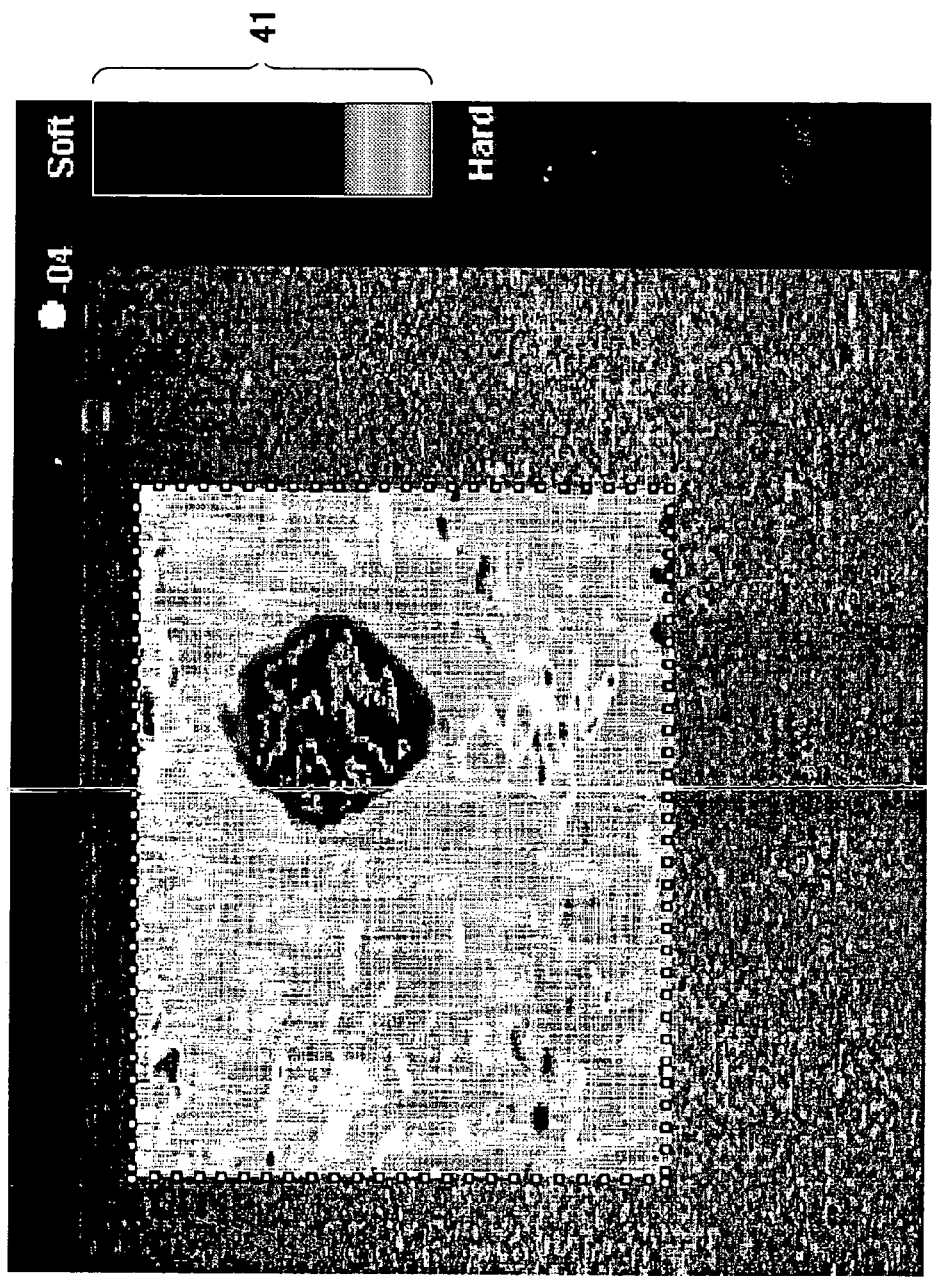
FIG. 12 is a diagram showing examples of image display operation according to the sixth embodiment.
Figure 13:
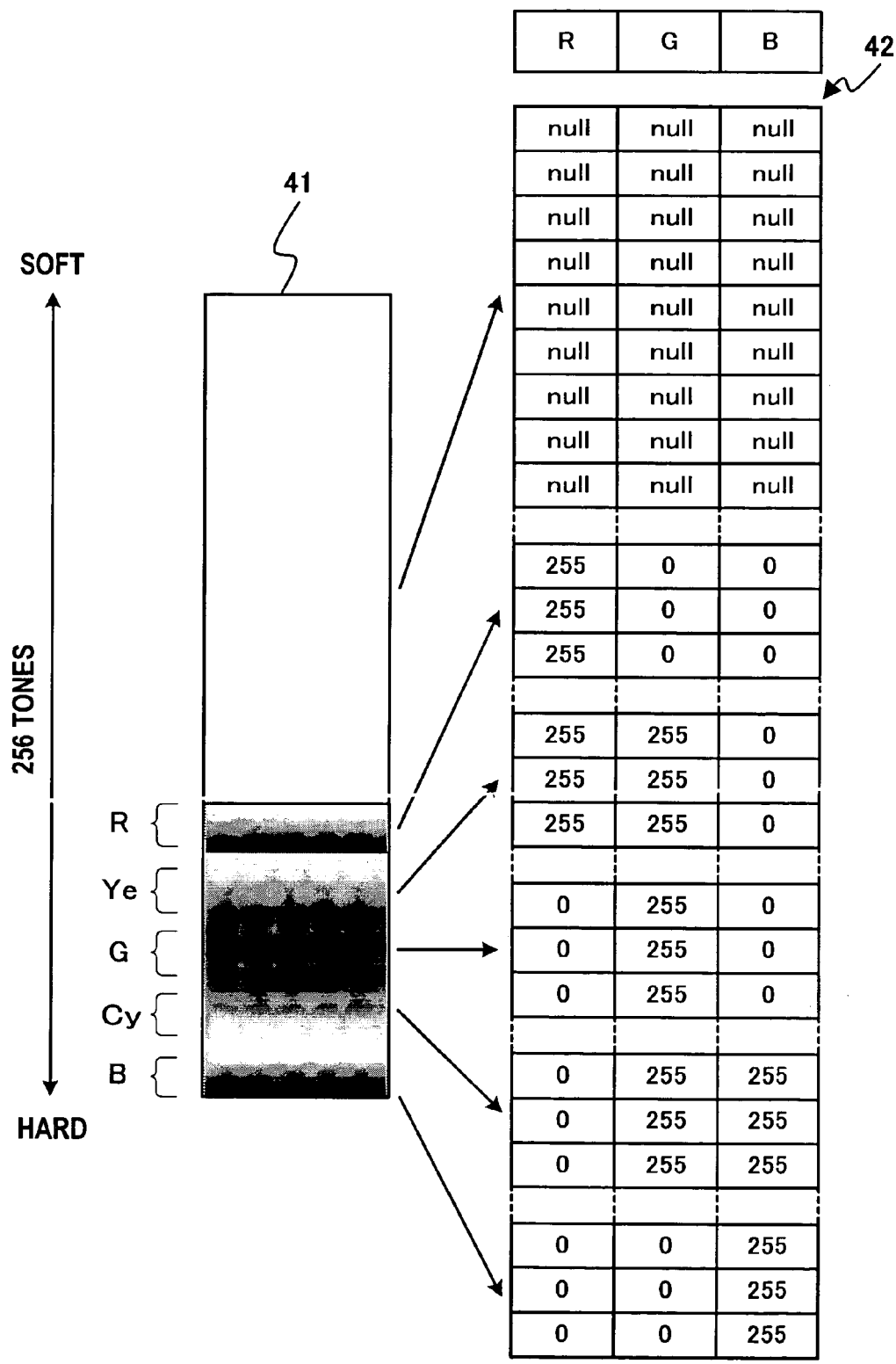
FIG. 13 is an explanatory diagram of a corresponding relationship between a color bar and hue information on a color conversion table according to the seventh embodiment.

FIGS. 12 and 13 show the color bar 41 and the color conversion table 42 according to the seventh embodiment. The color bar 41 according to the seventh embodiment is obtained by assigning the hue information to one portion of 256 tones. FIG. 13 is a diagram showing the details of the color bar 41 and the color conversion table 42. The color bar 41 according to the seventh embodiment is obtained by changing the color conversion table 42 from the operating unit 17 so that the hue information is added only to the region with desired hardness, null data is stored to a region other than the region with desired hardness, and the hue information is not added to the region other than the region with desired harness. As mentioned above, in order to specifically display a region of high interest, the color bar 41 shown in FIG. 8 is compressed and the hue information is assigned only to the region with hardness of high interest. The region having the assigned null data becomes the elastic image with transparency of 100%. Note that the color bar 41 may be compressed as shown in FIG. 10 or 11 and, alternatively, a single color may be assigned. As a consequence thereof, the hue information can be added only to a region to be specifically observed, the visibility can be improved.

According to the first to seventh embodiments, the components of the frame data of the elasticity and the hue have been described with the RGB-signal system. However, the present invention is not limited to this and the hue information may be added with another signal system (e.g., YUV-signal system).

Further, according to the first to seventh embodiments, the assignment of color codes of red R, green G, and blue B in the color conversion tables 31 and 41 is arbitrarily varied depending on the strain or the elastic modulus. Thus, the elastic information on the tissue, such as a soft or hard region and the level of the elastic modulus, can be displayed for easy identification in accordance with examiner's desire.

The invention claimed is:
1. An ultrasonic imaging apparatus comprising:
an ultrasonic probe that receives and sends ultrasonic waves from/to an object;
an ultrasound image structuring unit configured to generate an ultrasound image on the basis of a reflected echo signal received by the ultrasonic probe;
an elastic image structuring unit configured to obtain a strain or an elastic modulus of the elasticity of the object, of a region corresponding to the ultrasound image on the basis of the reflected echo signal, and to generate a color elastic image;
a display configured to overlay the color elastic image on the ultrasound image, or arrange the ultrasound image and the color elastic image for side-by-side viewing, and to display the resultant image on a screen; and
a setting unit configured to allow selectable setting of a corresponding relationship between a hue of the color elastic image displayed on the screen and the level of the strain or elastic modulus, wherein
the color elastic image is displayed with a same hue assigned to all levels of a range of levels where the strain or the elastic modulus is larger or smaller than a preset level of the strain or the elastic modulus;
the corresponding relationship between the hue of the color elastic image and the level of the strain or elastic modulus set by the setting unit is displayed on the screen with a color bar; and
with the color bar, an amount of the strain or the elastic modulus above the preset level and an amount of the strain or the elastic modulus below the preset level are displayed with different hues and the boundary between the hue having the amount of the strain or the elastic modulus above the preset level and the hue having the amount of the strain or the elastic modulus below the preset level is displayed with another hue.

2. An ultrasonic imaging apparatus according to claim 1, wherein the boundary between the hue having the large amount of the strain or the elastic modulus, and the hue having the small amount of the strain or the elastic modulus, is movably formed with the setting unit.

3. An ultrasonic imaging apparatus according to claim 1, wherein a boundary region of the hue different from the hue of the periphery, is settably formed at an arbitrary position of the color bar with the setting unit.

4. An ultrasonic imaging apparatus according to claim 1, wherein the color elastic image has a peripheral region including a setting value of the amount of the strain or the elastic modulus with the hue different from the hue of another region.

5. An ultrasonic imaging apparatus according to claim 4, wherein the hue of the peripheral region has a tone in accordance with the level of the amount of the strain or the elastic modulus.

6. An ultrasonic imaging apparatus according to claim 1, wherein the elastic image structuring unit comprises:
- a color conversion table that is rewritable, and sets a relationship between the level of the amount of the strain or the elastic modulus and the color of the color elastic image;
- a calculator configured to calculate an amount of the strain or the elastic modulus of the elasticity of the object of a region corresponding to the ultrasound image, on the basis of the reflected echo signal; and
- a color image generator configured to read the color corresponding to the obtained amount of the strain or the elastic modulus from the conversion table, and generate a color elastic image indicating the distribution of physical quantities, and
- wherein the color conversion table is rewritten in accordance with an instruction input from the setting unit.

7. An ultrasonic imaging apparatus according to claim 6, wherein the elastic image structuring unit displays, on the screen of the display unit, a color bar indicating a corresponding relationship between the level of the amount of the strain or the elastic modulus and the hue of the color elastic image, set to the color conversion table.

8. An ultrasonic imaging apparatus according to claim 1, wherein the color elastic image is displayed for at least one of a hard region with a high elastic modulus and a soft region with a low elastic modulus.

9. An ultrasonic imaging apparatus comprising:
- an ultrasonic probe that receives and sends ultrasonic waves from/to an object;
- an ultrasound image structuring unit configured to generate an ultrasound image on the basis of a reflected echo signal received by the ultrasonic probe;
- an elastic image structuring unit configured to obtain a strain or an elastic modulus of the object of a region corresponding to the ultrasound image on the basis of the reflected echo signal, and to generate a color elastic image;
- a display configured to overlay the color elastic image on the ultrasound image, or arrange the ultrasound image to the color elastic image for side-by-side viewing, and to display the resultant image on a screen; and
- a setting unit configured to allow selectable setting of a corresponding relationship between a hue of the color elastic image displayed on the screen and a level of the strain or the elastic modulus, wherein the setting unit assigns the hue of the color elastic image so as to prevent the display from displaying a neutral portion in a color conversion table;

the corresponding relationship between the hue of the color elastic image and the level of the strain or elastic modulus set by the setting unit is displayed on the screen with a color bar; and with the color bar, an amount of the strain or the elastic modulus above the preset level and an amount of the strain or the elastic modulus below the preset level are displayed with different hues and the boundary between the hue having the amount of the strain or the elastic modulus above the preset level and the hue having the amount of the strain or the elastic modulus below the preset level is displayed with another hue.

\* \* \* \* \*